(12) United States Patent
Ruetenik (10) Patent No.: US 10,154,938 B2
(45) Date of Patent: Dec. 18, 2018

(54) PORTABLE ICE SPA

(71) Applicant: Monty L. Ruetenik, Clear Lake City, TX (US)

(72) Inventor: Monty L. Ruetenik, Clear Lake City, TX (US)

( * ) Notice: Subject to any disclaimer, the term of this patent is extended or adjusted under 35 U.S.C. 154(b) by 599 days.

(21) Appl. No.: 14/821,709

(22) Filed: Aug. 8, 2015

(65) Prior Publication Data
US 2016/0051400 A1 Feb. 25, 2016

Related U.S. Application Data

(60) Provisional application No. 62/041,049, filed on Aug. 23, 2014.

(51) Int. Cl.
| | | |
|---|---|---|
| *A61F 7/00* | (2006.01) |
| *A61H 9/00* | (2006.01) |
| *A61F 7/10* | (2006.01) |
| *A61H 33/00* | (2006.01) |
| *A61H 35/00* | (2006.01) |
| *A61H 33/04* | (2006.01) |

(52) U.S. Cl.
CPC ............... *A61H 9/005* (2013.01); *A61F 7/10* (2013.01); *A61F 7/103* (2013.01); *A61H 33/0087* (2013.01); *A61H 35/006* (2013.01); *A61F 2007/0043* (2013.01); *A61F 2007/0045* (2013.01); *A61F 2007/0091* (2013.01); *A61H 2033/048* (2013.01); *A61H 2201/0214* (2013.01); *A61H 2201/165* (2013.01); *A61H 2201/1642* (2013.01)

(58) Field of Classification Search
None
See application file for complete search history.

(56) References Cited

U.S. PATENT DOCUMENTS

| | | | | |
|---|---|---|---|---|
| 7,204,041 B1 * | 4/2007 | Bailey, Sr. | ........... | A43B 3/0005 36/1 |
| 7,219,449 B1 * | 5/2007 | Hoffberg | ............... | A43B 1/0054 36/29 |
| 8,166,734 B2 * | 5/2012 | Ruetenik | ............... | A01K 13/007 168/2 |
| 8,832,971 B2 * | 9/2014 | Heid | ..................... | A43B 1/0081 36/11.5 |
| 9,022,957 B2 * | 5/2015 | McKay | .................. | A61F 7/0053 297/423.1 |
| 9,055,732 B1 * | 6/2015 | Ruetenik | .................. | A61D 9/00 |
| 2009/0113759 A1 * | 5/2009 | Heid | ..................... | A43B 1/0081 36/92 |
| 2010/0057171 A1 * | 3/2010 | Stephens | ................ | A61F 5/3761 607/108 |
| 2010/0145421 A1 * | 6/2010 | Tomlinson | ................ | A61F 7/02 607/104 |
| 2011/0093050 A1 * | 4/2011 | Damkoehler | ............. | A61F 7/02 607/111 |
| 2011/0137304 A1 * | 6/2011 | Mayberry | ............... | A01L 15/00 606/22 |

(Continued)

*Primary Examiner* — Stephen R Crow
(74) *Attorney, Agent, or Firm* — Douglas Baldwin (57) ABSTRACT

An ice boot spa system that is lightweight and portable to allow leg and ankle cooling in a mineral bath and optionally means to secure a foot to the spa and to provide proper foot support. It enables a portable means for cryotherapy that is self-contained and that can be used, in some embodiments, without an external power source or refrigeration means.

16 Claims, 7 Drawing Sheets

(56) References Cited

U.S. PATENT DOCUMENTS

| | | | |
|---|---|---|---|
| 2015/0119772 A1* | 4/2015 | Ruetenik | A01K 13/007 601/149 |
| 2016/0051400 A1* | 2/2016 | Ruetenik | A61H 9/005 601/15 |
| 2017/0027734 A1* | 2/2017 | Riordan | A61F 5/0109 |
| 2017/0280682 A1* | 10/2017 | Ruetenik | A01K 13/007 |

* cited by examiner

PORTABLE ICE SPA

CROSS REFERENCE TO RELATED APPLICATIONS

This application claims benefit of Provisional Application Ser. No. 62/041,049 filed Aug. 23, 2014, the contents and disclosures of which is incorporated herein by reference in its entirety for all purposes

BACKGROUND

Field of Invention

This invention is in the field of cold mineral spas for use in cryotherapy. More specifically it is a portable ice boot spa useful for treatment of sore or damaged limb tissue and muscles.

Background

According to Dr Warren Gregson PhD, Principal Lecturer in Exercise Physiology Programme Leader B.Sc. (Hons) Sports Science; School of Sport & Exercise Sciences; Liverpool John Moores University Liverpool; "The application of localised cold or cyrotherapy is well established as a therapeutic modality for the treatment of acute soft-tissue injuries. By decreasing local tissue temperature around the injured site, cryotherapy reduces the inflammatory response in injured tissue as well as decreasing local oedema formation, swelling and pain and thus promotes recovery from soft tissue injury. Along with soft-tissue injury, inflammation is also integral in the development of exercise-induced muscle damage that frequently occurs following unaccustomed or high intensity eccentric exercise. Anecdotal reports have therefore suggested that cooling the previously active limbs via cold water immersion may also serve as an effective recovery strategy for athletes undertaking high intensity exercise. Recent reports in the scientific literature have shown that cold water immersion may alleviate the physiological and functional deficits associated with exercise-induced muscle damage and enhance recovery following high intensity exercise. As a consequence, cold water immersion is now becoming widely adopted by athletes in both training and competition in an attempt to enhance the recovery process. Despite evidence supporting the use of cold water immersion as a recovery modality, little is currently known with respect to the precise physiological mechanisms through which it mediates its effects." See the information at the website www.coldspa.com/Clinical.html.

Large fixed no-portable ice spas are commercially available and are becoming widely used, particularly for athletes. As reported on its website at www.coldspa.com "ECB, Founded in 2001, started out by making and operating Cold Spas for horses. The use of cold salt hydrotherapy in the equine world was not a new one—trainers have used cold hosing, stood horses in rivers and walked them in the sea for hundreds of years with remarkable results. ECB manufactured a unit that could be easily installed in yards and give trainers easy access to cold salt hydrotherapy."

"ECB began to hear of stories of people using the horse spas. In one case where the spa had been installed in an equine rehabilitation yard the owner was treating up to 500 people a week. The interest in the benefits for humans using Cold Spas has been phenomenal. Sports teams began to take an interest and add Cold Spas to their facilities. These include the prestigious Welsh Rugby Team and Northampton Saints. From this ECB saw a need for a small ice bath that could be easily installed and used without the need for continuous water changing or large quantities of ice and also giving the option of adding salt in to the water."

However, these spas are large and are not portable. What is needed is a lightweight portable self-contained ice spa that can be used anyplace and without need for an external source of power or cooling equipment. The present invention is such a spa.

SUMMARY

An object of the present invention is to provide a relatively simple, lightweight, portable spa system to allow leg and ankle cooling in a mineral bath and optionally means to secure the foot to the spa and to provide proper foot support.

It is also an object of this invention to be able to provide a portable means for cryotherapy that is self-contained and that can be used, in some embodiments, without an external power source or refrigeration means.

BRIEF DESCRIPTION OF FIGURES

The Figures represent embodiments and aspects of the invention and are not intended to be limiting of the scope of the invention.

DETAILED DESCRIPTION

Ice baths and ice spas have become popular and a have been shown to be very beneficial in preventing and treating soft tissue injuries and soreness resulting from exercise and athletic activity. The conditions that can be treated, the treatment parameters, the expected results and the science behind the effectiveness of cold water spa treatment are extensively documented in the literature and need not be repeated here.

Some advantages of the use of the ice spa boots of this invention are that they are lightweight, portable, can be used where there is no electrical power, easily cleaned and optionally provide shock absorbing foot support not available in any currently available systems. The large commercial spas now available contain large amounts of water that is generally recycled—it is usually filtered and chlorinated for cleaning. This is expensive and likely not very effective in removing fungi and other harmful contaminants. The portable spa of the present invention avoids this problem.

The spa of this invention may be used almost anywhere including in locker rooms, on the sidelines of athletic events, when traveling and at home.

The present invention is an assembly, system and method of use for a portable ice spa. The spa consists, in some embodiments, of a reservoir for containing coolant with means for injecting air or other gas into the reservoir. Optionally, the system will include a shock adsorbing elastomeric pad or foot support disposed in the bottom of the reservoir. In one embodiment the spa is a boot made of a waterproof flexible material having a shock absorbing orthotic gel pad and/or gel foot retaining means disposed in the bottom of the boot spa. An optional drain valve with a flexible conduit that can be connected to an air pump to provide a flow of air into liquid contained in the reservoir is also provided. The reservoir will contain coolant (preferably water) with minerals such as sea salt and optionally added magnesium salts. Suitable coolant liquids should be capable of dissolving sea salt and magnesium salts.

Coolant may or may not be circulated. Water with ice is the preferred coolant since the spa is intended to be portable and ice is readily available and inexpensive. A refrigerant means for chilling and circulation coolant is acceptable and within the scope of the invention but less portable, more expensive and generally requires an external source of electric power. Ice and water requires no electric power and allows great portability for the system. Circulation and air supply may be supplied by battery power.

In broad scope the invention is an assembly for cryotherapy in a cold mineral coolant liquid bath. In one embodiment the invention is an ice spa assembly comprising;

a reservoir for containing coolant having a closed bottom and open top;

a bottom sole structure for the reservoir, to which the bottom of the reservoir is attached; and means for injecting air or other gas into the lower section of the reservoir.

There may also be a shock absorbing pad and/or foot retaining structure disposed in the bottom of the reservoir with means to hold it into place. The foot retaining means will keep the boot spa attached to a user's foot and leg when the leg is lifted.

More specifically, in a preferred embodiment, the reservoir is a boot having sides and bottom made of water retaining fabric, a bottom sole structure that has a solid bottom and side walls extending entirely around the circumference of the bottom sole, and may have means to inject air into the lower section of the reservoir. Optionally, the boot has at least one zipper and at least one batten pocket extending from the top of the boot downward.

In use, the reservoir is partially filled with water and crushed ice and the air circulated into a port (or through a conduit entering the top of the boot and extending to near the bottom) at the lower end of the boot. Sea salt is added to the coolant in the reservoir and optionally magnesium salt. Sea salts contain a number of elements other than sodium chloride that are beneficial in the spa treatment including potassium, calcium chloride and bromides. Sea salts with varying amounts of other compounds are available commercially. Magnesium salts that are soluble in water are also available. Magnesium sulfate and magnesium chloride are useful. In general it is desirable that the salt concentration be about twice that of sea water. A concentration of about 1 to 10% salt has been shown to be effective. About 2% should be sufficient in most uses. Since the effectiveness of the osmotic effect of the minerals is determined by concentration (and temperature) optimum salt levels may be determined by simple experimentation. The salts may be prepackaged in the correct amount to add to a predetermined amount of water in the boot reservoir. Coolant temperatures of about 32-40° F. are desirable. Treatments (legs in coolant) of about 20-40 minutes have been found effective.

Figure 1:
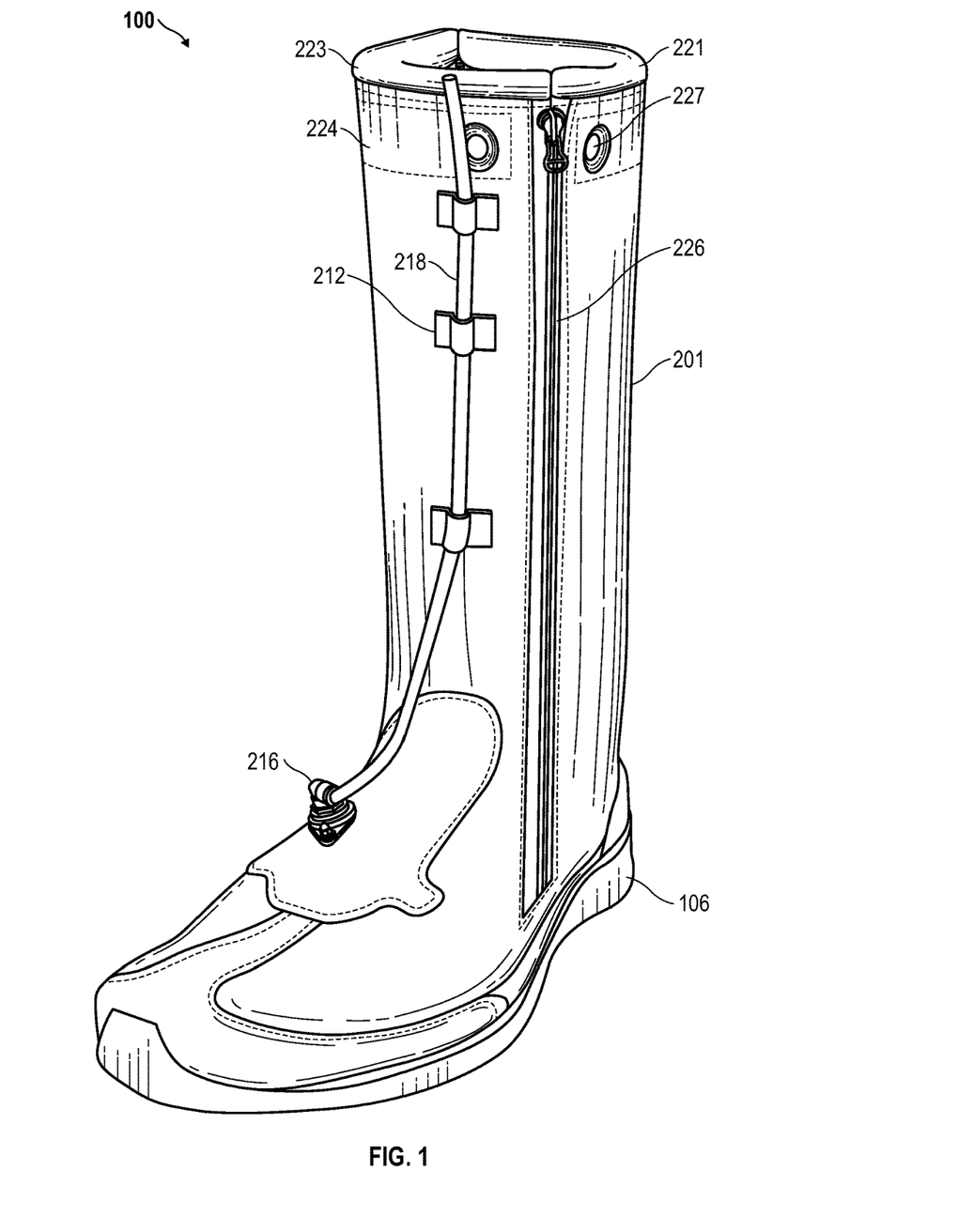
FIG. 1 is a side sectioned view of an ice spa assembly of an embodiment of the invention.
Figure 2:
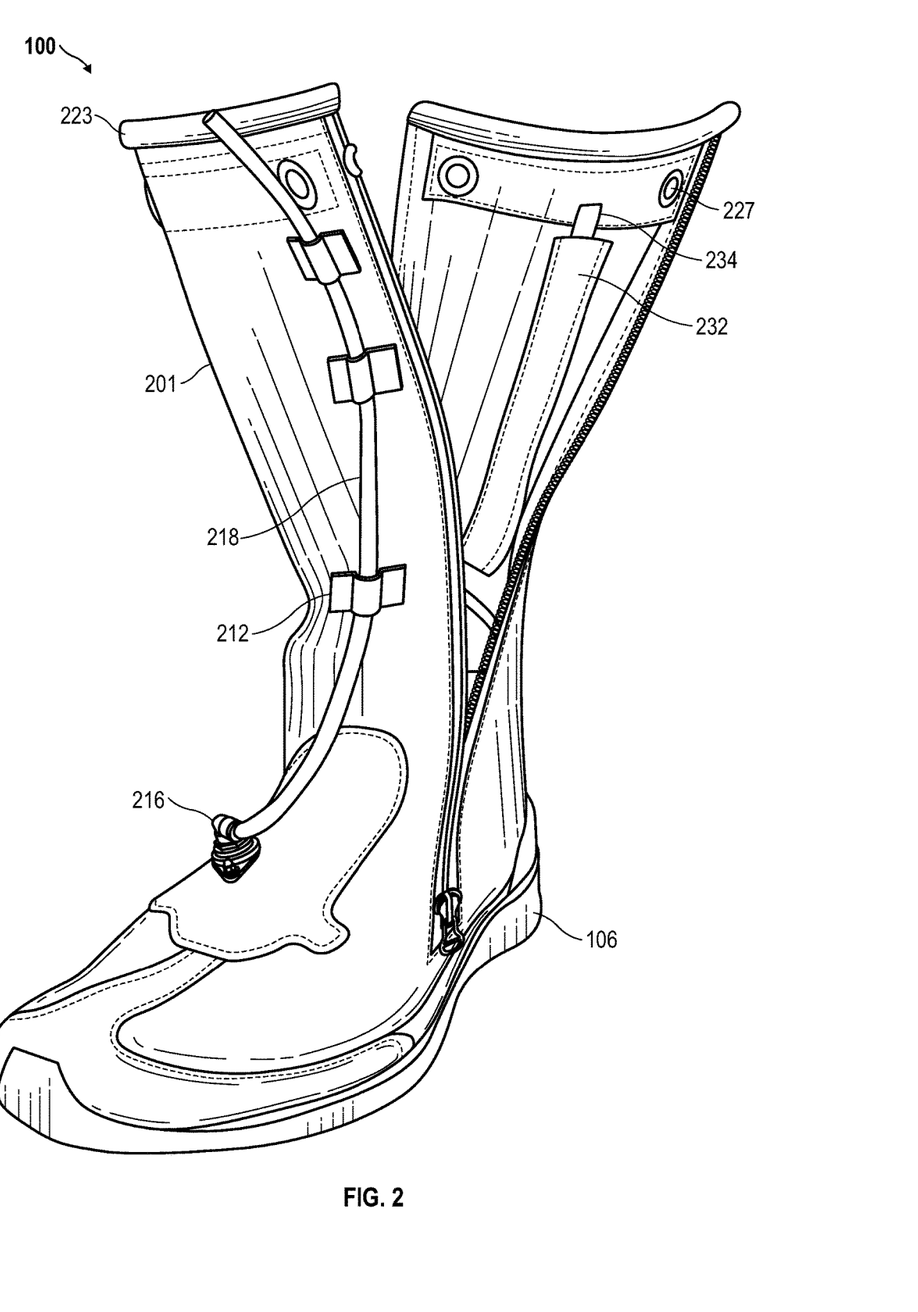
FIG. 2 is a perspective view of an embodiment of the invention showing the sides of a boot opened.
Figure 3:
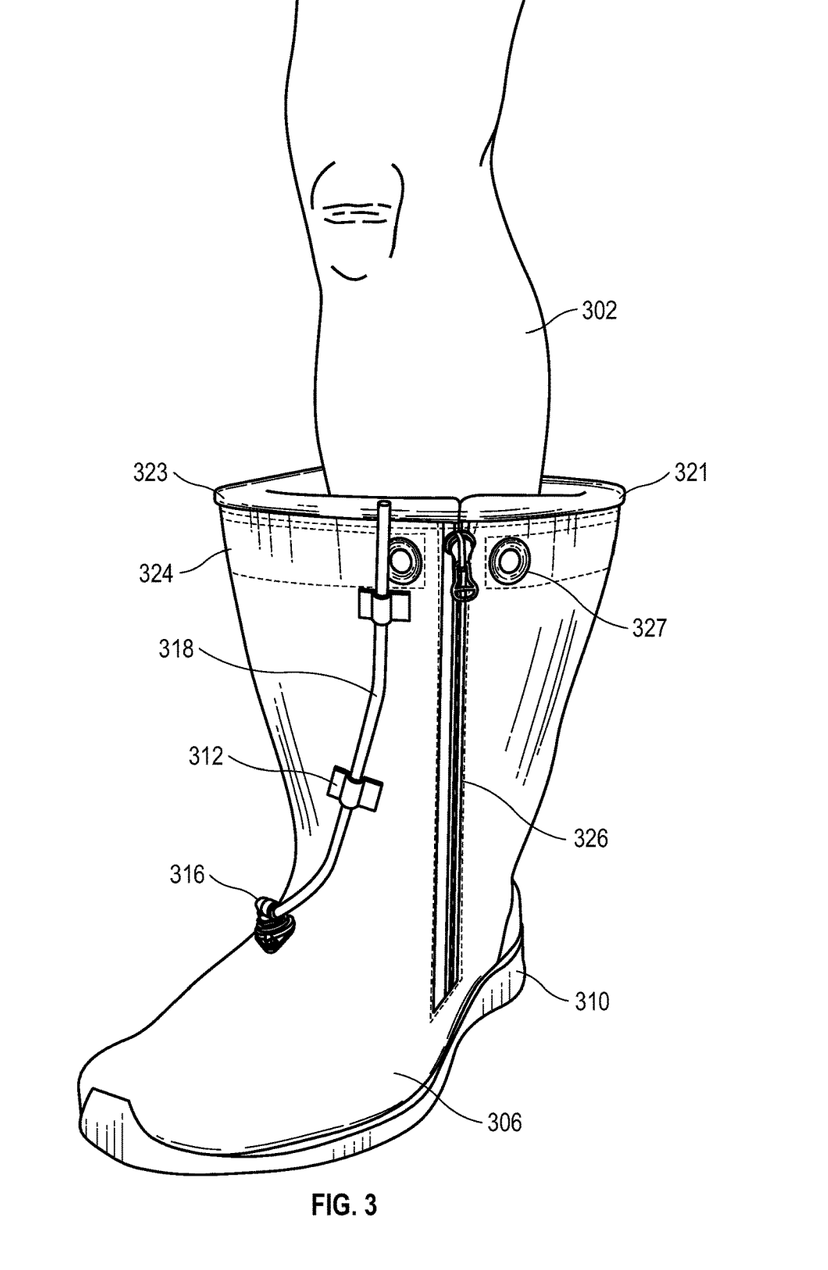
FIG. 3 is a perspective view of an embodiment of the invention.

Embodiments of the invention with a boot reservoir are illustrated in FIGS. 1-3. The boot may be made of a water-proof fabric and desirably has at least one zipper, and preferably two, to facilitate placing the leg into the boot and the boot retaining means. The boots, in preferred embodiments, have a drain, 216, with a plastic conduit, 218, attached The boot will, in some embodiments, also have releasable means to attach to the leg to the boot to prevent stepping out of the boot, i.e. to allow the boot to be lifted with the leg as more fully described below. A boot of lighter weight fabric material with or without side openings can be rolled down from the top to allow inserting a leg more easily and to facilitate access the leg retention means in the bottom inside of the boot.

Referring to FIGS. 1-2 there is shown a coolant boot assembly having a coolant boot 201 attached into a recess in a bottom sole structure 106. The bottom sole structure walls may be attached to the sides of the lower portion of the water retaining material of the boot by adhesive or sewing or both. Conventional and customary means of attaching upper fabric to the soles of athletic shoes is suitable and within the scope of means contemplated in this invention. The sole structure will generally be larger than normal since (normal size to fit a particular user's foot) it must contain leg retention means (described below) and be sufficiently large to allow circulation of coolant around the foot.

Inside the boot 201 is, optionally, disposed an elastomeric shock-absorbing orthotic pad (described in or detail below). Shock adsorbing pads such as silicone gel pads such as Dr. Scholl's™ as currently used in shoes are suitable but should be water proof and sufficiently robust to withstand soaking in salt water for sustained periods. Other shock adsorbing pads and structures are described below.

The boot is conical shaped and open at the top. The boot may also have a drain (216 in FIGS. 1-2) to enable coolant (such as cold water) to be removed. Drain valves such as those used to drain boats that have a plug that is retained in the drain hole are suitable. Water may be drained through the drain valve to a flexible (preferably transparent) tube (218 in FIGS. 1-2). The drain is shown on top of the boot front but may be located at any convenient place of the lower section of the boot. The conduit tube can be loosely attached (212) to the side of the boot as shown FIGS. 1-2. The tube will be attached, for example, to an air pump to bubble air through the liquid in the boot and may be used to agitate and to circulate water in the boot and around the legs and foot. Coolant (and/or air) may also be circulated into and out of the boot by suitable pumping means through the tube 212 or through other conduits that are placed at the top of the boot and extending downward inside the boot structure. The tube, 212, facilitates bubbling air or other gas into the liquid in the boot to mix the coolant, oxygenate the coolant and provide a massaging action. The tube, 218, when attached to the drain 216 and disposed alongside the boot as shown in FIGS. 1-2 can be used as a handy sight glass to determine the liquid level in the boot.

Again referring to FIGS. 1-2 a prototype boot is conical shaped vertically for better mobility and ease of use. In general the boot will be even more conical that it appears in FIGS. 1-2 as illustrated in FIG. 3. The conical shape is especially important if the boot has no side opening but is adapted to be rolled down to fit the foot into the boot.

Waterproof zippers, 226 are optionally located around the sides of the boot 201. Two zippers placed opposite each other have performed well in trials of a prototype and are preferred. One or more zippers are suitable in appropriate circumstances. These zippers allow the boot walls, 201, to be opened to allow the foot to be fitted into and secured in the boot and be properly placed a leg retention means located in the inside bottom of the boot. Items 232 (FIG. 2) are pockets extending substantially the length of the boot wall into which are placed stiff battens (234) to hold the boot upright and prevent sagging.

In a prototype, the walls, 201, were made of a Polyurethane (TPU) coated fabric and the batten pockets and zippers were rf welded to the TPU fabric. The relative locations of the zippers (210) and batten pockets, 232, shown in the Figures are illustrative only and have proved useful in a prototype, but other locations, and number of zippers and batten pockets may also be varied as desired and such other arrangements are within the scope of this invention. The important aspect is that the boot walls may be opened (or able to be folded down) to fit the foot into the boot and secure it to the boot bottom. The removable battens hold the boot upright in use but can be removed when the sides are opened or rolled down. Other forms of opening devices, rather than zippers that will allow the boot to hold water for a substantial period are also within the scope of the invention. Lighter weight fabric may be used to allow a boot without zippers or other side opening to be rolled down to allow access to the boot bottom.

The top of the boot has a fold, 221 and 223, that provides a smooth top side and may be filled with foam such as a foam rope. The fold is made of polymer fabric that can provide a soft, smooth surface to prevent chafing or otherwise damaging the skin of the leg. This may be a foam "rope" such as used in concrete crack patches that is encased in the boot flexible material or other attached fabric. A desirable fabric for use in this anti-rub section may be made of Ultra-high-molecular-weight polyethylene such as Dyneema™ fabric.

Items 227 are optional grommets that are useful but not an essential component of the invention. The grommets will allow the boot to be suspended by cords or the like to keep the user from stepping out of the boot. Since the boot may be filled with ice particles it can be important that the foot not be lifted to allow ice to get under the foot.

FIG. 3 illustrates another embodiment of the boot spa system shown in FIGS. 1-2. This version is shorter and more tapered at the top. This embodiment is otherwise similar to that of FIGS. 1-2. The boot body 306 is disposed into the recess of the sole structure 310. There are zippers, 326, grommets, 327, a drain 316 with conduit 318 that may be attached to the boot walls as shown in 312. The band 324 is a reinforcing piece at the top of the boot. There is also an anti-rub section 321 at the top of the boot. Air (or other gases) is injected into the boot coolant by attaching an air pump to the conduit 218 (or 312). An air pump such as those available for hydroponics and weighing about 4-8 pounds works well. The air pump can be battery operated and fitted with a connection for an external 12 volt power source or one that operates on 110 or 220 volt circuits. The pump may be housed in a watertight housing or case and adapted to be hung on straps or harness to, for example, be suspended from a user's shoulders—the grommets will facilitate this type suspension.

Prototype boots have been made with a 36 inches top circumference and a height of about 28 inches but may be any convenient size. For boots that are extended above the knee, the height will be about 28 to 36 inches. The general size of the users will determine the appropriate size—if for football players the boots will be much larger than ones suited for gymnast. These dimensions are illustrative only and may vary as desired.

The boot may be constructed of any suitable material, such as fabrics and flexible polymer materials capable of retaining water. Simple plastic boots such as polyethylene or polypropylene may be used but generally will not be sufficiently strong and will make it difficult to attach components. In a prototype a TPU coated fabric (for example polyester or polyester or Nylon™) is used to good effect. The fabric is commercially available from numerous sources including Mesa Laminated Fabrics (www.mesafabrics.com) and Eastex Products (www.eastexproducts.com). In a prototype, Mesathane 6036 from Mesa Laminated Fabrics (35 or 45 gage) works very well. The TPU coating allows RF welding of components that is an important consideration in constructing batten pockets and attaching zippers described below. Water retaining nylon fabric as used in tents and the like is also suitable.

The base sole of some embodiments (see FIGS. 1-3) is attached to the lower section of the cooling boot or made as an integral part of the boot structure. Attachment may be accomplished by adhesive and/or mechanical mean. For example, the sole may be first attached by a suitable adhesive then sewn to the lower portion of the cloth boot. The methods of attaching upper fabric sides to athletic shoes are entirely suitable and sufficiently well-known so detailed description is unneeded here. Details of such sole are disclosed for equine boots in U.S. Pat. No. 9,055,732 can easily be adapted to the somewhat different shape of the boots of this invention. See particularly col. 9, lines 22-61 and associated Figures. The disclosure and drawings of U.S. Pat. No. 9,055,732 are incorporated herein for all purposes. The structure of the sole structure is important in providing side support for the bottom of the boot and when applicable giving side support to orthotic pads or foot retaining means disposed in the boot. In these embodiments the sole plate is a separate molded piece. The sole plate helps to hold the orthotic pad in position and is preferably walled around the entire circumference. The sole structure is important in confining the circumference of an orthotic pad. If a relatively "soft" pad is used (as is usually desirable) the weight of the user will flatten the pad or foot retaining structure and, if there were an opening in the sole plate the pad would be extruded out the opening. It is especially important that the bottom circumference of the boot be entire. By having the sole plate wall entirely surrounding the circumference, the pad is held in place and will conform to the shape of the foot—and adapt to the shape of the foot as the users moves. These features provide a desirable massaging similar to the effect of having the user stand in loose sand. The sole plate is also desirably sloped front to back on the bottom to provide an easy break-over as is described in more detail (for horse boot but equally applicable for the present invention) in U.S. Pat. No. 8,220,231 issued Jul. 17, 2012. Similar suitable sole plates are described and shown in; US 2011/00673661 published Mar. 24, 2011; U.S. Pat. No. D565,256 issued Mar. 25, 2008 and U.S. Pat. No. D616,614 issued May 25, 2010. The descriptions and Figures of these patents are incorporated herein by reference for all purposes. The sloped sole allows a whole roller motion of the sole to eliminate trauma of a user moving or turning.

In other embodiments the sole plate is curved in the manner of a "Masai Barefoot Shoe" such as described in PCT/2008/006940, Pub. Jun. 4, 2009 and U.S. Pat. No. 7,793,434, issued Aug. 14, 2010, the description and shapes of the sole of which are incorporated herein by reference.

Removable Attachment of Leg to Boot

An important aspect of embodiments of the ice boot spa of this invention is the inclusion of means to removably secure the foot and leg to the boot so that when the leg is lifted the boot will remain attached. The means to hold the foot and boot together are desirably as open as possible to facilitate coolant flow around the foot. Therefore, it is preferred that the means be more like a sandal than a shoe so the foot is better exposed to the fluid coolant.

Figure 9:
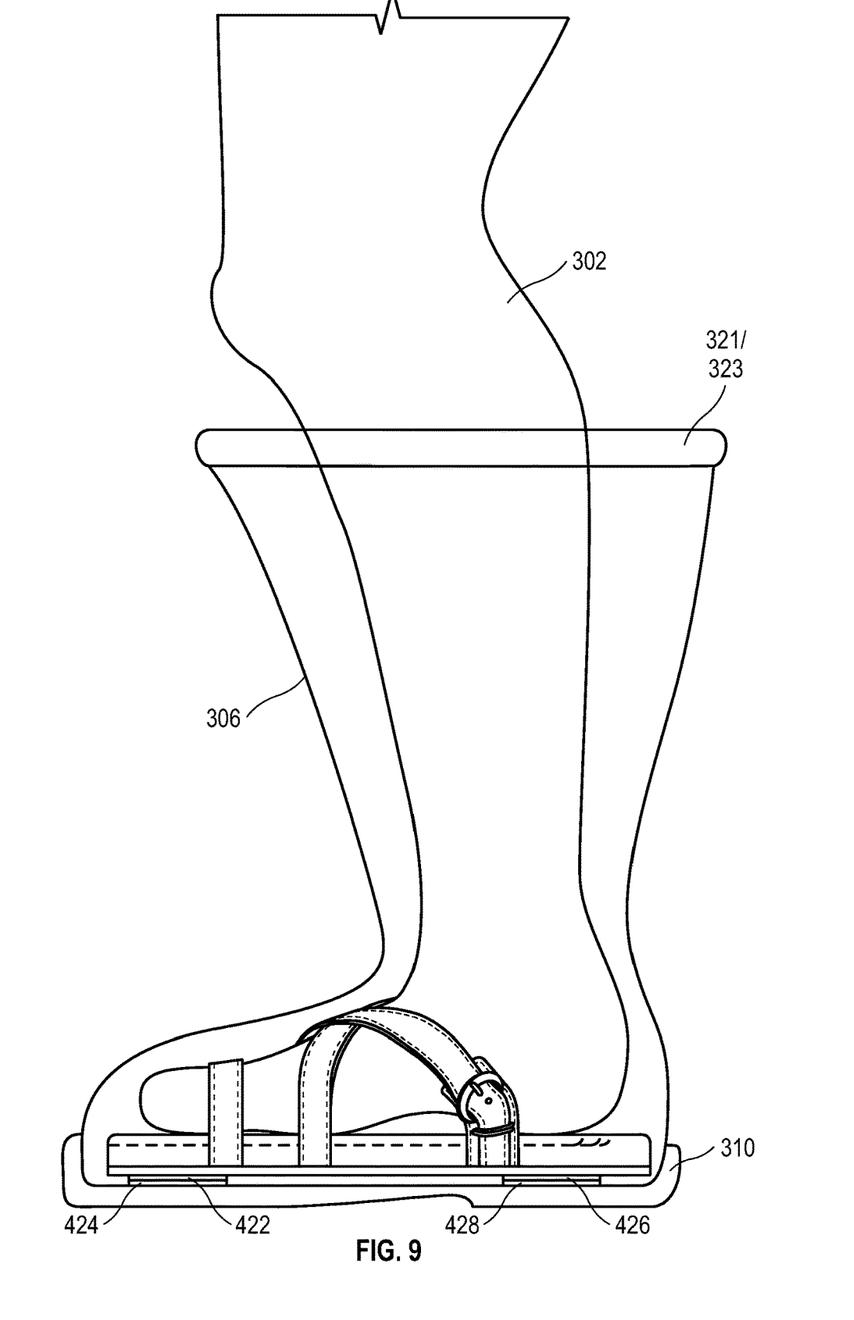
FIG. 9 is a side view of another foot attachment showing a foot in the attachment means of an embodiment of invention.

In one foot retaining means straps attached to bottom sides and/or back of the inside of the boot and can be tied, buckled, or hook and loop attached around the ankle of the leg. FIG. 9 shows such a strap with sandal but the strap may be used alone without the sandal insert. The front of the foot held in place by the shape of the boot or by cup shaped piece disposed in the toe section of the boot such as in a sandal.

It is desirable that the holding means (as a sandal removably attached to the inside bottom of the boot) is easy for the foot to slip into but secure enough to allow walking with the spa boot and foot securely holding together. There are a number of releasable boot attachments available as will be apparent to those skilled in the art. For example it will be suitable to use a sole boot connection means as used in ski boot attachments and in the Korker™ Omnitrax™ and L Kling-On™ systems for fishing waders. See www.korkers.com. An open sandal such as plastic garden sandals or Clogs™ will be useful especially if there is provide a tie, lace or hook and loop system in the rear bottom of the boot to strap around the ankle (see FIG. 9). These boot sole connectors will allow quick connection and release but also allow the leg and boot to be connected. If the spa boot is zippered then more secure means can be used. For example the holding means can be a sandal with straps that lace, buckle or attaches by hook and loop attachments (as Velcro™ like straps—better hook and loop means are available than commercial Velcro™ products)).

Figure 4:
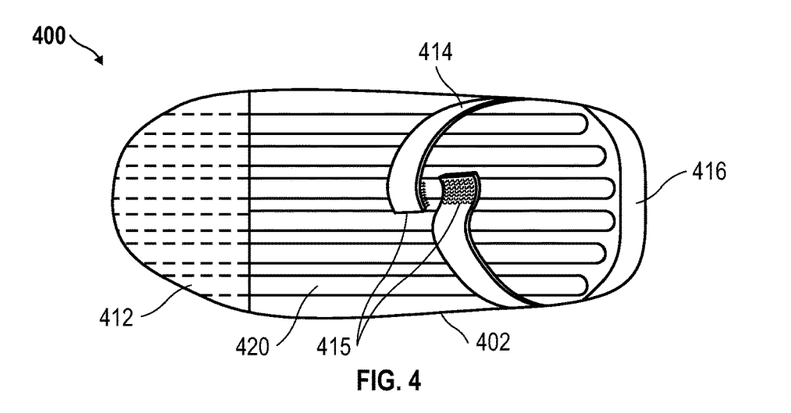
FIG. 4 is a top view of an embodiment of a foot attachment means of the invention
Figure 5:
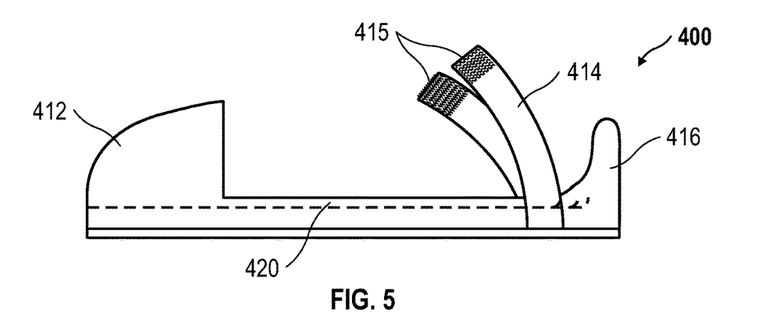
FIG. 5 is a side view of the foot attachment means of FIG. 4 of an embodiment of the invention.
Figure 6:
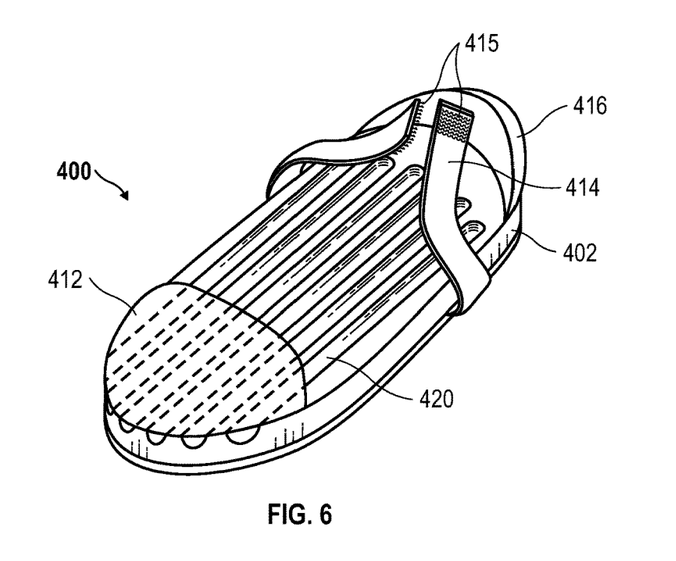
FIG. 6 is a perspective view of the foot attachment means of the embodiment of FIGS. 4 and 5 of an embodiment of the invention.
Figure 7:
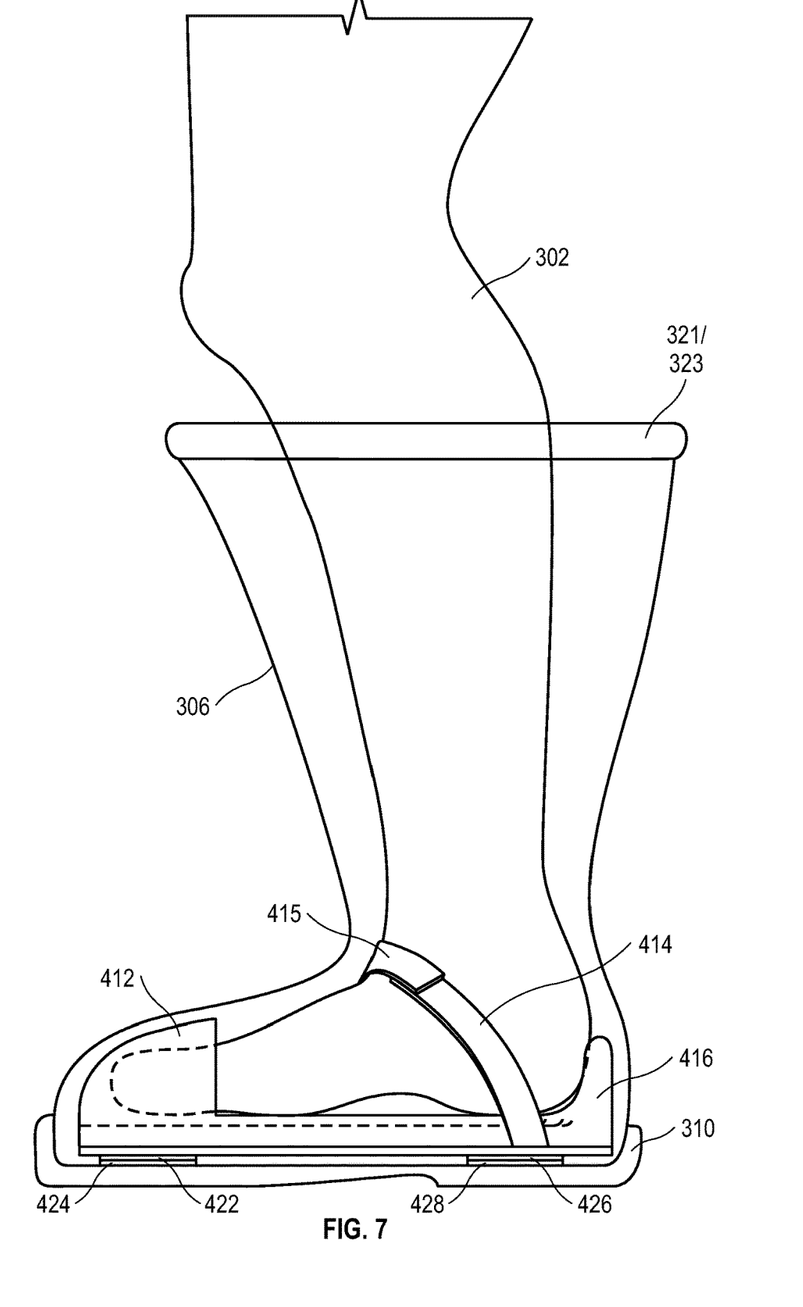
FIG. 7 is a side view of the foot attachment of the embodiment of FIGS. 4 and 5 showing a foot in the attachment means of an embodiment of invention.
Figure 8:
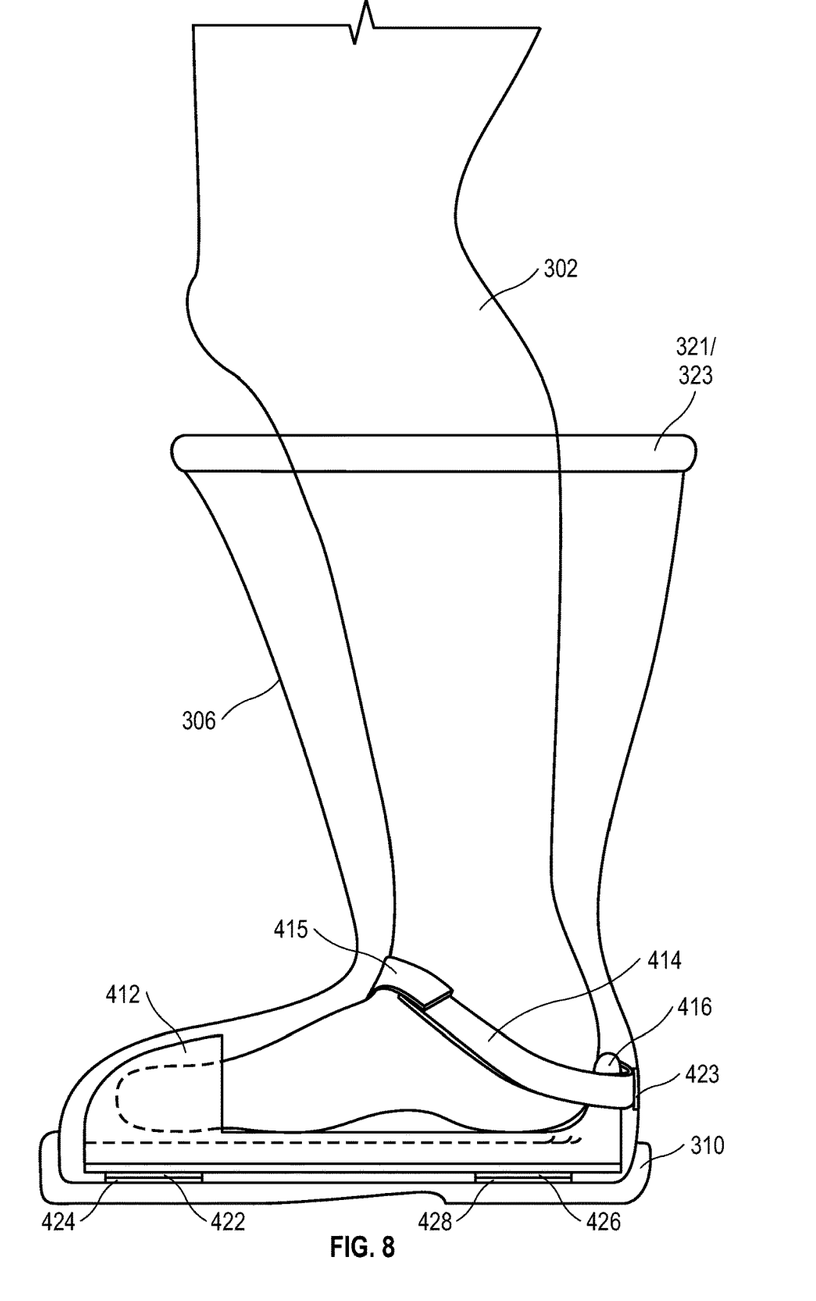
FIG. 8 is a side view of the foot attachment of the embodiment of FIGS. 4 and 5 showing a foot in the attachment means of another embodiment of invention.

A number of means for securing the foot to the boot are illustrated in FIGS. 4-9. Referring to FIGS. 4-6, a foot retaining insert embodiment is illustrated. The insert is preferably made of an elastomeric material such as polyurethane gel. The polyurethane can be made by molding in an open mold or it and versions made of other polymers can be injection molded or produced by other polymer forming techniques well known to those skilled in the art. FIG. 4 is a top view of one embodiment—FIG. 5 a side view and FIG. 6 a perspective view. The insert 400 has a toe piece 412 to contain the toes of a user and make the insert fit more securely on the foot. A similar insert without the toe piece that relies on the the shape of the boot to retain the toes is also within the scope of the invention. There is a back rest 416, a base 402 and straps, 414 and 415, for securing the insert around the ankle of a user. There may also be grooves 420 in the base of the insert to allow coolant to better circulate under the user's foot. The straps as shown are secured with a hook and loop attachment (such as Velcro™), but may be secured by any other suitable means as by a buckle, snaps, laces, self-adhesives and the like. The straps may be permanently attached to the base 402 or made detachable. The straps as shown are attached to the bottom sides of the rear section of the insert. However, they may also be attached to the lower rear of the boot as shown in FIG. 8. In FIG. 8 the strap are shown, as is preferred, detachably attached to the rear section of inside the boot 423. By being detachable other structural configurations of the insert may be facilitated and more easily changed. For example, it may be desirable to have a number of different sizes of insert (for different users) but use the same strap. Or it may be desirable to replace straps without need to replace the inserts. Referring to FIGS. 7 and 8 it can be seen that the inserts can be attached to the bottom of the boot by attachment means 424, 425, 426 and 428. Hook and loop attachment is shown, but other means such as laces, buckles, ties, adhesive and sewing. Snaps and the like may also be used. Hook and loop attachment is preferred. Rather than straps as shown there may also be side pieces that fit around the ankle and laced or attached together with hook and loop attachment must like the sided of a shoe opening. Such a sides are preferably detachable.

FIG. 9 shows another means to hold the foot into the boot spa. There is shown a sandal that is disposed in the boot and removably attached to the bottom of the boot by attachment means 424,422,426 and 428 (as in FIGS. 7 and 8). Attachment by hook and loop attachment with one half attached to bottom of boot and other to bottom of sandal is very suitable. Attachment at both ends preferred. A preferred sandal is made of polymer (plastic) material but can be leather or other flexible, suitable sandal material.

In another embodiment the holding means may be a harness that is removably attached around the ankle and to hook and loop straps attached to the inside bottom of the boot as in the equine bot spa described in U.S. Pat. No. 9,055,732, the disclosure and Figures of which are incorporated herein by reference.

It is preferred that the elastomer inserts described above (FIGS. 4-8) be shaped to conform to the inside circumference dimensions of the boot base sole. In most cases it is desirable that the inserts and pads (if used) be a relatively soft and deep elastomer—Shore 00 of 5 to 60 hardness and of about 0.50 to 2.0 inches thickness. The soft pad/insert will conform to the shape of the inside of the base sole and reshape itself as the user shifts its weight since the pad is soft and pliable and constrained by the wall of the boot. The soft pads should generally extend to the edges of the inside walls of the bottom sole and the walls must be of sufficient strength to constrain the gel pad. The inserts and pads may be single density or duel density. In a dual density insert or pad the front and rear section will have Shore 00 hardness between 5 and 70, but will be different front and rear. For example, a duel density insert or pad may have a front section of Shore 00 hardness of 30 and a rear section hardness of 60 Shore 00. Or, conversely, it may have a front section hardness of 50 and a rear section hardness of 20 Shore 00. The choice of hardness and the arrangement in the duel density insert or pad is determined by the desired outcome. However it should be noted that these hardness ranges are not just optimum or desired ranges but definitional of the structure. Polymer elastomers span a huge range of hardness from very soft to metal hardness. The very soft and very hard are not suitable for this invention. The principle importance of the soft deep insert/pad is that it lets the user seek the most comfortable position and thus minimize stress and damage to sore or damaged muscles. The pad and inserts of such elastomeric gel provides an easy foot retention means and a therapeutic gel massaging action for the spa boot.

Shock Adsorbing Pads

As noted above, conventional shock adsorbing pads are suitable for use in the boot spa. They will be laid in the bottom of the boot a in a manner similar to that described for the foot attachment means above. They may be laid in the boot or in the insert or sandal or other foot attachment means. Pads may be made of any suitable shock absorbing material such as elastomeric polymer material that provides flexibility, shock absorbency, some degree of elasticity, resilience and has dimensional stability. Polyvinyl chloride PVC, polysilicone and similar elastomers are suitable.

The boot assembly or system as described in the embodiments above may be fitted with an air pump (battery or power operated) to inject air through the tube 216 and valve 218 into liquid in the boot reservoir.

Coolant, may be as simple as crushed ice in water, which in the open top boot will be very suitable and is preferred. Other coolants may also be used, particularly if the coolant is externally cooled and circulated in the coolant bag or boot. Suitable coolants should have good thermal conductivity, a low flash (or vaporization temperature) point, be non-corrosive, inexpensive and readily available and be able to dissolve sea salt. Some useful coolants include, but are not limited to: chilled water, ethylene glycol, propylene glycol, methanol/water, ethanol/water, calcium chloride solution, potassium formate/acetate solution. The choice of coolant can also be made to affect the temperature of the coolant. Temperatures to which the leg can be cooled are not extreme—e.g. it is unlikely that the temperatures below about zero (0°) F. will be desirable Generally coolants will be above about 32° F.

Fitting the Boot on a Leg

In a boot with zippers (or other openings) opening on the sides, the sides are open and laid back. The leg is guided into the boot and leg retention means fitted and/or attached. If there is no opening in the sides of the boot its walls may be rolled down and the harness connected as described above.

Method

The method of the invention comprises fitting a leg needing cryotherapy treatment into cooling boot assembly described herein, filling the cooling boot with coolant (and replenishing the coolant as it gains temperature) and minerals for sufficient time to and temperature to effect measurable cooling of the leg and foot, and, optionally, injecting a gas into the coolant. The minerals that are generally most beneficial are sea salt and magnesium compounds. It has been reported that in human medicine, the general consensus is that 20 to 30 minutes at a time for cooling is sufficient. Allowing the leg and foot to warn after a period of chilling increases blood flow and help sweep away harmful enzymes caused by the body's reaction to the injury or stress. According to ECB website, www.coldspa.com, "The cold water works in several ways. Firstly the cold will help take out heat and inflammation. Secondly it helps control enzyme deterioration on tendon and ligaments in the early stages of injury, thirdly it massively increases circulation. When people are in the spa they undergo vascular constriction, but when people get out of the spa they experience the 'Hunting Rush', which is a blood rush to warm the area."

In use, the boot reservoir is partially filled with water and crushed ice and the air circulated. A suitable method of filling the boot is to fill the bottom of the boot to above the ankle (about one gallon in the prototypes), add salt then add water and ice to fill the boot. Adding water first keeps the ice from lodging under the foot and allows good mixing of the salts. Sea salts contain a number of elements other than sodium chloride that are beneficial in the spa treatment including potassium, calcium chloride and bromides. Moreover, the source of sea salt is important in selection of trace minerals. For example, it is reported that waters from the Dead Sea are unique in that they contain 27% of various salts as compared to 3.1-3.8% in normal sea water. Further, while sodium accounts for approximately 80% of the salt content of normal sea water, it comprises much less of the salt total in water from the Dead Sea. The balance of the salts in Dead Sea water is magnesium, potassium, calcium chloride and bromides. Sea salts from various sources and with varying amounts of minerals are available commercially.

Magnesium salts that are soluble in water such as magnesium sulfate and magnesium chloride are useful. As with sea salts magnesium salts from different natural sources are available.

In general it is desirable that the salt concentration be about that of sea water −3.1-3.8% (35 gm./l). A concentration of about 0.2 pounds of sea salt and 0.3 pounds of magnesium salt has been shown to be effective. Since the effectiveness of the osmotic effect of the minerals is determined by concentration (and temperature) optimum salt levels may be determined by simple experimentation. It has been reported that concentrations of 2 and 7.5% sea salt in water is very effective in reducing pain and increasing mobility in human trials. Machtey, Dr. I. 1982, *Dead Sea Balneotherapy in Osteoarthritis, Proc. International Seminar on Treatment of Rheumatic Diseases.*

The salts may be prepackaged in the correct amount to add to a predetermined amount of water in the boot reservoir. Coolant temperatures of about 32-40° F. are desirable. Treatments (legs in coolant) of about 20-40 minutes have been found effective. A short prototype of the boot assembly will contain about 2.25 gallons of coolant with a leg in the boot. A taller prototype holds about five (5) gallons. A boot that extends above the knee will contain even more liquid.

In the foregoing specification, the invention has been described with reference to specific embodiments thereof. It will, however, be evident that various modifications and changes can be made thereto without departing from the broader spirit and scope of the invention as set forth in the appended claims. The specification is, accordingly, to be regarded in an illustrative rather than a restrictive sense. Therefore, the scope of the invention should be limited only by the appended claims.

The invention claimed is:

1. An ice spa boot assembly comprising a reservoir for containing coolant comprising;
   a cylindrical structure having a closed bottom and open top and side walls, the reservoir having an upper section and lower section, wherein the lower section extends outward laterally from the top section and is in the shape of a human shoe;
   a bottom sole plate having a solid bottom and side walls, onto which the bottom portion of the reservoir is attached; and
   a conduit for injecting fluid into means for injecting air into a closable opening in the lower section of the reservoir.

2. The spa assembly of claim 1 wherein the reservoir is made of a flexible polymer coated fabric.

3. The spa of claim 2 comprising means to removably secure the bottom of the boot to a leg.

4. The spa of claim 2 comprising at least one zipper in the side of the boot extending from the top downward.

5. The spa assembly of claim 2 comprising at least one batten pocket on the inside wall of the boot extending from the top downward.

6. The spa assembly of claim 2 comprising a shock adsorbing pad disposed in the bottom of the boot in a manner to be in contact with a user's foot when a foot is placed in the reservoir.

7. The spa assembly of claim 6 wherein the shock adsorbing pad is an elastomer gel shaped as the bottom sole of the boot and sized to be substantially the size of the inside bottom of the sole.

8. The spa assembly of claim 1 wherein the reservoir has a bottom and side and rear walls comprising straps permanently or detachably attached to the rear bottom or back bottom wall of the reservoir.

9. The spa assembly of claim 1 comprising means to secure a foot into the reservoir.

10. The spa assembly of claim 1 wherein the reservoir is a boot comprising sides and bottom of water retaining fabric, a bottom sole is semi-rigid and has a solid bottom and side walls extending entirely around the circumference of the sole and has at least one zipper at least one batten strap extending from the top of the boot downward and means to removably secure an elastomeric pad to the bottom of the boot.

11. A method of treatment of and legs, ankles and feet needing treatment comprising fitting a leg that will benefit from cryotherapy treatment into a spa assembly, filling the spa assembly reservoir with water for sufficient time and at a temperature to effect measurable cooling of the leg wherein the spa assembly comprises;
   a reservoir for containing coolant comprising;
   a cylindrical structure having a closed bottom and open top and side walls, the reservoir having an upper section and lower section, wherein the lower section extending out laterally from the top section and is in the form of a human shoe;
   a bottom sole plate having an entire bottom and side walls, onto which the bottom of the reservoir is attached; and,
   a conduit for injecting fluid into means for injecting air into a closable opening in the lower section of the reservoir.

12. The method of claim 11 also comprising a shock adsorbing pad disposed in the bottom of the boot in a manner to be in contact with the user's foot.

13. The method of claim 11 wherein the water contains salt selected from the group consisting of sea salt and magnesium salt or both is added to the coolant, air is circulated into the coolant in the lower portion of the assembly reservoir.

14. The method of claim 11 where water is first added to the boot to at least ankle height, salt added and then additional water and ice added to substantially fill the boot.

15. The method of claim 11 where the leg is placed in the spa reservoir for 10 to 50 minutes, removed and allowed to warm.

16. The spa assembly of claim 8 wherein the means comprise a elastomeric structure with a toe cap, heel stop and straps to wrap partially around an ankle or a sandal detachably-disposed in the bottom of the reservoir.

* * * * *